(12) United States Patent
Wright (10) Patent No.: US 7,806,936 B2
(45) Date of Patent: Oct. 5, 2010

(54) BOWED FEMORAL SLEEVE

(75) Inventor: Abraham P. Wright, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/551,086

(22) Filed: Oct. 19, 2006

(65) Prior Publication Data

US 2008/0097614 A1   Apr. 24, 2008

(51) Int. Cl.
*A61F 2/38* (2006.01)
(52) U.S. Cl. .................. 623/20.15; 623/20.25
(58) Field of Classification Search .......... 623/20.15, 623/20.34, 20.36, 22.41–22.43, 22.46, 13.18, 623/23.23, 23.24, 23.44, 23.46, 16.11, 18.11, 623/20.14, 20.35, 22.4, 23.11, 23.15, 23.42, 623/23.47, 20.19, 20.25–20.28, 22.45; 606/62
See application file for complete search history.

(56) References Cited

U.S. PATENT DOCUMENTS

| | | | |
|---|---|---|---|
| 4,068,324 A * | 1/1978 | Townley et al. .......... | 623/23.24 |
| 4,846,839 A | 7/1989 | Noiles | |
| 4,882,366 A | 11/1989 | Nelson et al. | |
| 5,011,496 A | 4/1991 | Forte et al. | |
| 5,782,921 A | 7/1998 | Colleran et al. | |
| 6,071,311 A | 6/2000 | O'Neil et al. | |
| 6,171,342 B1 * | 1/2001 | O'Neil et al. ............ | 623/20.15 |
| 6,527,807 B1 * | 3/2003 | O'Neil et al. ............ | 623/20.15 |
| 6,953,479 B2 * | 10/2005 | Carson et al. ............ | 623/20.15 |
| 7,189,261 B2 * | 3/2007 | Dews et al. ............... | 623/19.14 |
| 2003/0074079 A1 * | 4/2003 | McTighe et al. ......... | 623/22.42 |
| 2003/0204264 A1 * | 10/2003 | Stumpo et al. ........... | 623/20.36 |
| 2004/0254646 A1 * | 12/2004 | Stone et al. .............. | 623/23.15 |
| 2005/0107883 A1 * | 5/2005 | Goodfried et al. ........ | 623/20.15 |
| 2006/0173547 A1 * | 8/2006 | Ensign .................... | 623/20.15 |

FOREIGN PATENT DOCUMENTS

| | | |
|---|---|---|
| EP | 1398006 A2 | 3/2004 |
| EP | 1532945 A2 | 5/2005 |
| EP | 1623686 A2 | 2/2006 |

OTHER PUBLICATIONS

European Search Report dated Jan. 17, 2008, filed in Appl. No. 0725089.1-2310 (7 pages).

* cited by examiner

*Primary Examiner*—Corrine M McDermott
*Assistant Examiner*—Rebecca Straszheim
(74) *Attorney, Agent, or Firm*—Barnes & Thornburg LLP (57) ABSTRACT

A modular femoral joint prosthesis includes a femoral component having a post extending therefrom, a femoral stem, and a femoral sleeve configured to be coupled to the post of the femoral assembly and to the femoral stem. The femoral sleeve is bowed posteriorly in the sagittal plane.

7 Claims, 8 Drawing Sheets

BOWED FEMORAL SLEEVE

TECHNICAL FIELD

The present disclosure relates to medical devices, and more particularly to prosthetic joint components. In particular, the present disclosure relates to a femoral joint prosthesis for a knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer bearing positioned between the tibial tray and the femoral component. The femoral component generally includes a pair of spaced apart condylar portions, the surfaces of which articulate with corresponding surfaces of the polymer bearing. The femoral component has a stem or post that is implanted into the intermedullary canal of the distal end of the femur to provide stability. A femoral sleeve may be coupled to the femoral component in revision knee replacement procedures or other procedures involving a large intermedullary canal to facilitate additional fixation, for example. Typically, the femoral sleeve operates to fill in spaces or gaps at the opening of the intermedullary canal.

SUMMARY

The present invention comprises one or more of the features recited in the appended claims or the following features or combinations thereof.

According to one aspect of the present disclosure, femoral sleeve is configured to be coupled to both a femoral component having a post extending therefrom, and a femoral stem. The femoral sleeve includes a body having (i) a first bore configured to receive the post therein and (ii) a second bore configured to receive a portion of the femoral stem therein. The first bore defines a first longitudinal axis and the second bore defines a second longitudinal axis which intersects the first longitudinal axis to define an acute angle of intersection therebetween.

Illustratively, the acute angle of intersection is between 2-5°. Specifically, the acute angle of intersection is approximately 3°.

The first bore of the femoral sleeve may be formed in a distal end surface of the body to define a tapered inner surface while the second bore may be formed in a proximal end surface of the body to define a threaded inner surface. Alternatively, the second bore may define a tapered inner surface.

The body of the femoral sleeve may include a contoured outer surface defining a plurality of stepped sections. Illustratively, each stepped section is angled in relation to each other stepped section. The body may include four stepped sections.

Further illustratively, the body of the femoral sleeve includes a distal end surface which defines a distal plane and a proximal end surface which defines a proximal plane. The distal plane may intersect the proximal plane to define an acute angle of intersection therebetweeen.

The body of the sleeve may be bowed posteriorly in the sagittal plane

According to another aspect of the present disclosure, a modular femoral joint prosthesis includes a femoral sleeve having a first bore and a second bore. The femoral sleeve is bowed in a posterior direction. The joint prosthesis further includes a femoral component having an articulating condylar surface, a post having a first end secured to the femoral component, and a femoral stem. The femoral stem is configured to be implanted within the intermedullary canal of the distal end of a femur and includes a first end positioned in the second bore of the femoral sleeve and a second end extending proximally away from the femoral sleeve.

Illustratively, the first bore defines a first longitudinal axis and the second bore defines a second longitudinal axis which may intersect the first longitudinal axis to define an acute angle of intersection therebetween. The second longitudinal axis may also intersect an imaginary line extending perpendicularly from a plane defined by a distal surface of the femoral sleeve to define an acute angle of intersection therebetween. Further, the first longitudinal axis may be coaligned with the imaginary line. Alternatively, the first longitudinal axis may intersect the imaginary line. In some embodiments, the acute angle of intersection may be between 2-5°, while in other embodiments, the acute angle of intersection may be approximately 3°.

According to yet another aspect of the present disclosure, a femoral sleeve configured for use with a femoral stem and a femoral component having a post extending therefrom includes a first bore configured to receive the post therein and a second bore configured to receive the femoral stem therein. The femoral sleeve further includes a first stepped section defining a first imaginary line extending along an anterior surface of the first stepped section when viewed in cross section through the center sagittal plane of the femoral sleeve and a second stepped section defining a second imaginary line extending along an anterior surface of the second stepped section when viewed in cross section through the center sagittal plane of the femoral sleeve. The first imaginary line intersects the second imaginary line to define an acute angle of intersection therebetween.

Illustratively, this acute angle of intersection may be approximately 1°.

The femoral sleeve may further include a third and fourth stepped sections each defining respective third and fourth imaginary lines extending along respective anterior surfaces when viewed in cross section through the center sagittal plane of the femoral sleeve. The third imaginary line may intersect the second imaginary line to define a second acute angle of intersection between the second and third imaginary lines of approximately 1°. Further, the fourth imaginary line may intersect the third imaginary line to define a third acute angle of intersection between the third and fourth imaginary lines of approximately 1°.

Further illustratively, the first bore of the femoral sleeve may define a first longitudinal axis and the second bore may define a second longitudinal axis which is angled posteriorly in the sagittal plane relative to the first longitudinal axis.

The above and other features of the present disclosure will become apparent to those skilled in the art upon consideration of the following detailed description and accompanying drawings of illustrative embodiments exemplifying the best mode of carrying out the disclosure as presently perceived.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 1:
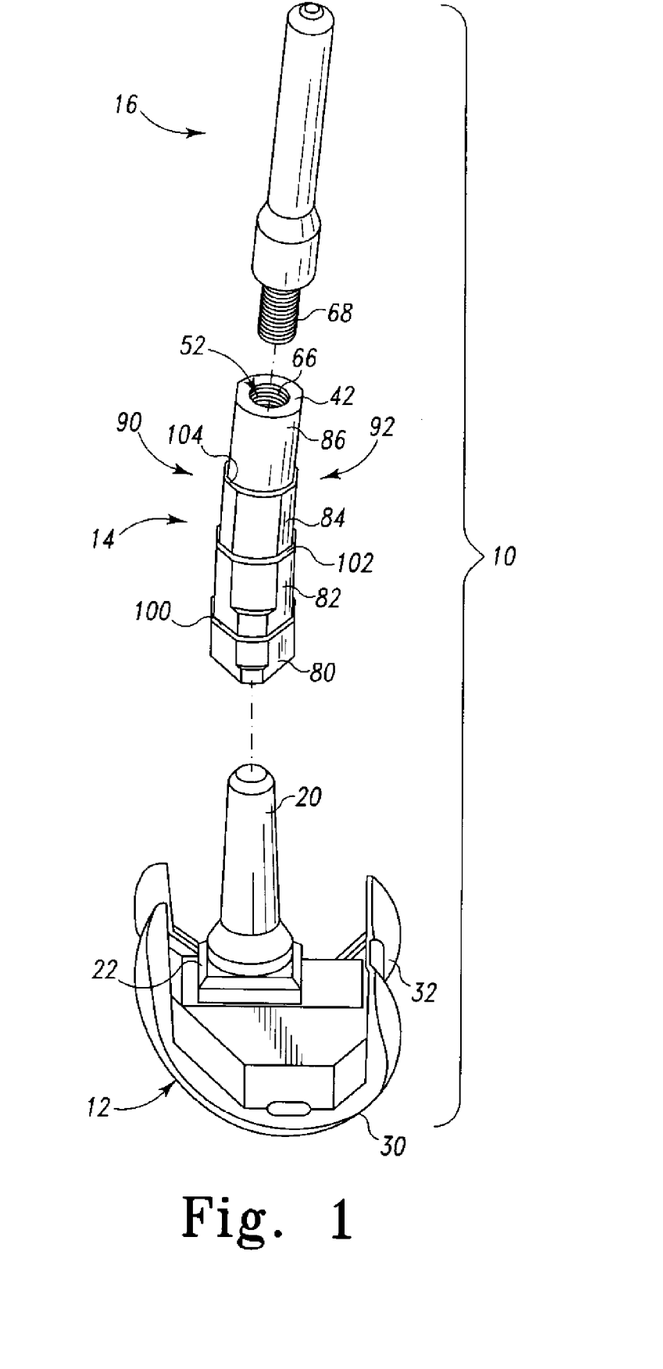
FIG. 1 is an exploded, perspective view of a modular femoral joint prosthesis.
Figure 2:
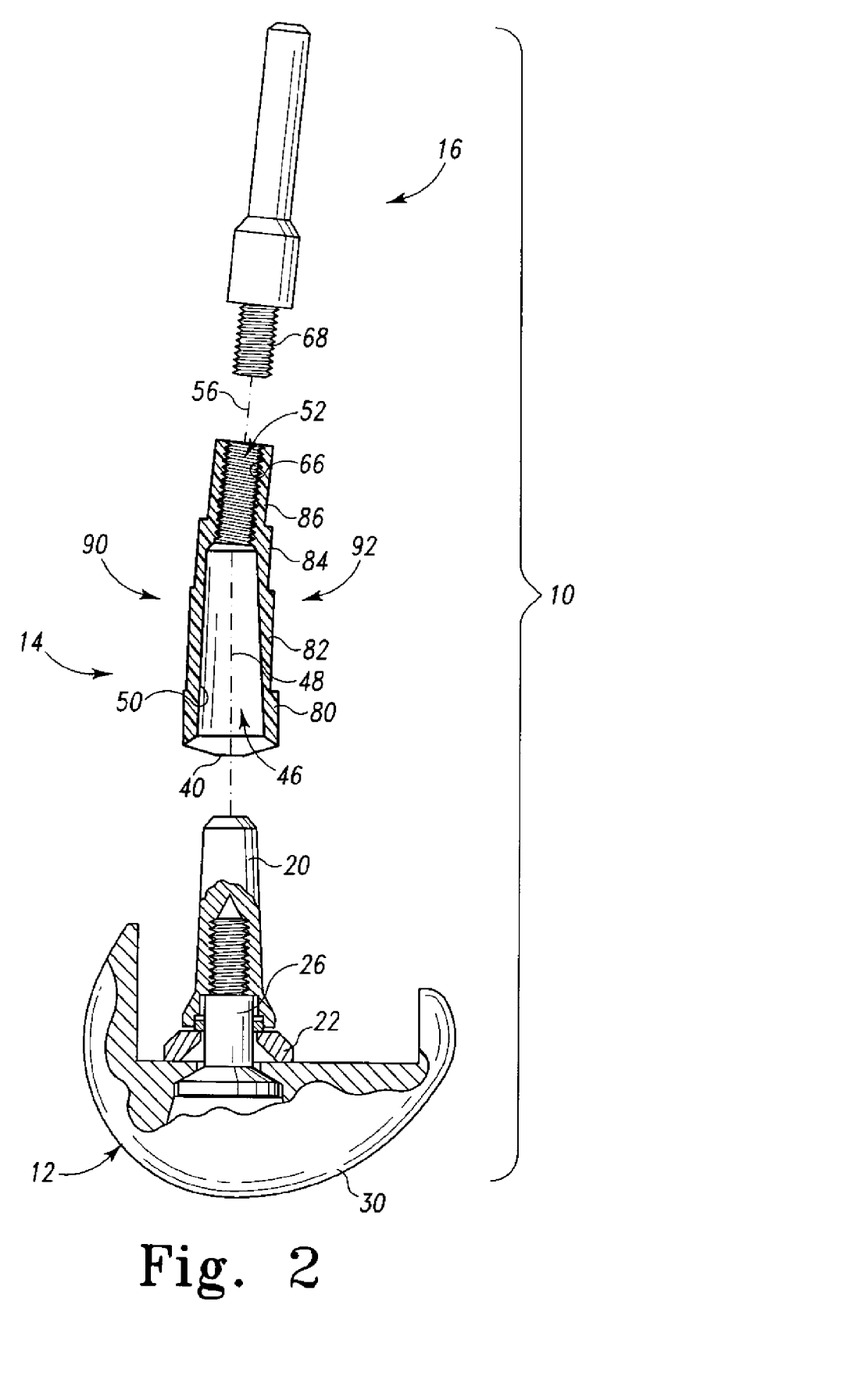
FIG. 2 is a side, sectional, exploded view of the modular femoral joint prosthesis of FIG. 1.
Figure 5:
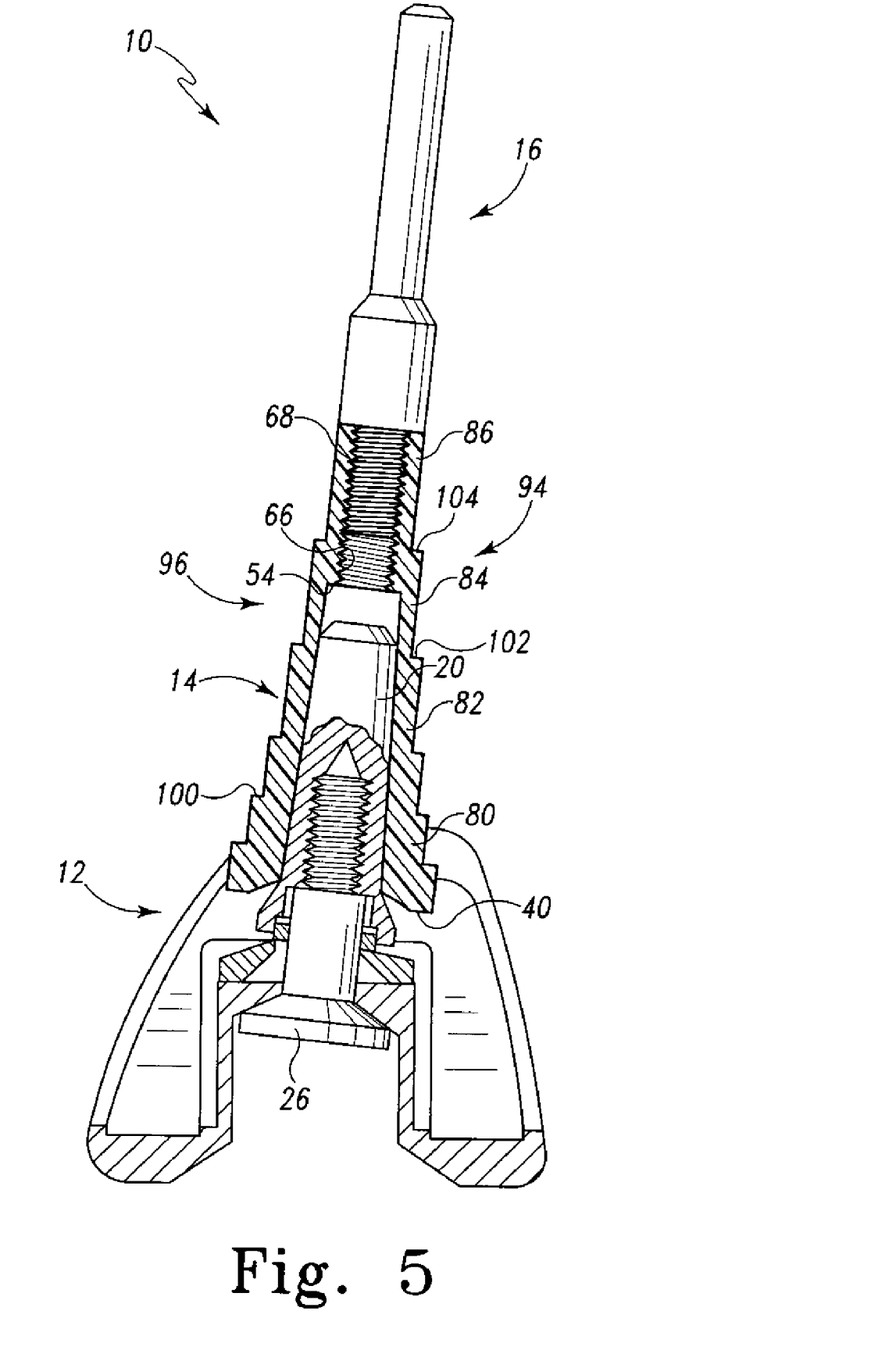
FIG. 5 is a front, sectional view taken along line 5-5 of FIG. 4.
Figure 7:
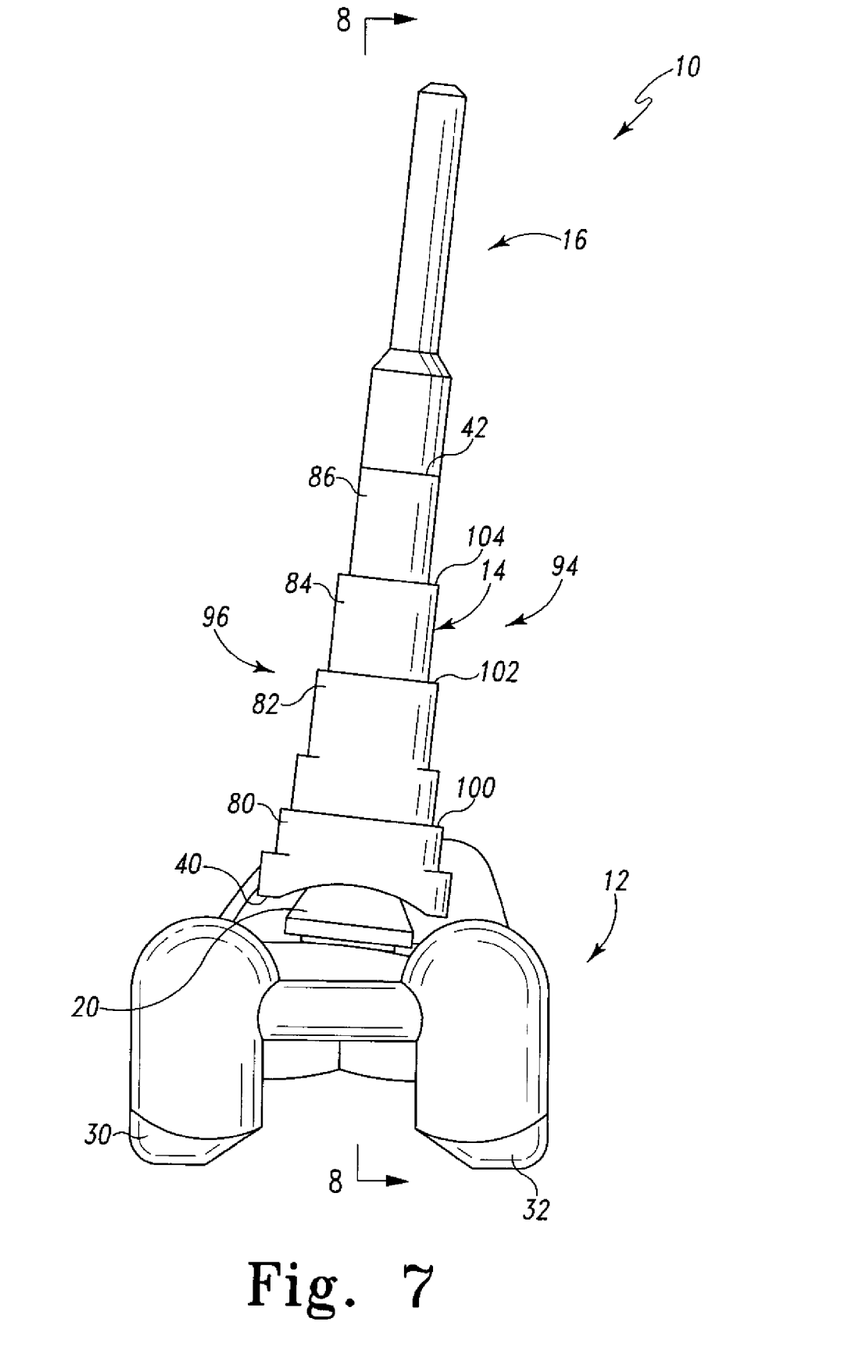
FIG. 7 is a front view of the assembled modular femoral joint prosthesis.

Looking to FIGS. 1 and 2, a modular femoral knee prosthesis 10 includes a femoral component 12, a femoral sleeve 14, and a femoral stem 16. Illustratively, the femoral component 12 has a Morse taper post 20 and a collar 22 secured thereto by a bolt 26. The post 20 is configured to extend in a proximal direction away from the femoral component 12 and is angled laterally with respect to the femoral component 12, as shown in FIGS. 5 and 7, for example. Illustratively, while the femoral component 12 is modular and includes the post 20 coupled thereto, it is also within the scope of this disclosure to include a femoral component having a post formed integrally therewith.

The femoral prosthesis 10 is configured to be implanted into a prepared distal end of the patient's femur (not shown) during a total knee replacement or revision knee surgery. The femoral component 12 is configured to emulate the configuration of the patient's natural femur. As such, the curved, condylar surfaces 30, 32 of the femoral component 12 articulate on a pair of corresponding bearing surfaces of a tibial component implanted into a prepared proximal end of the patient's tibia (not shown).

Figure 3:
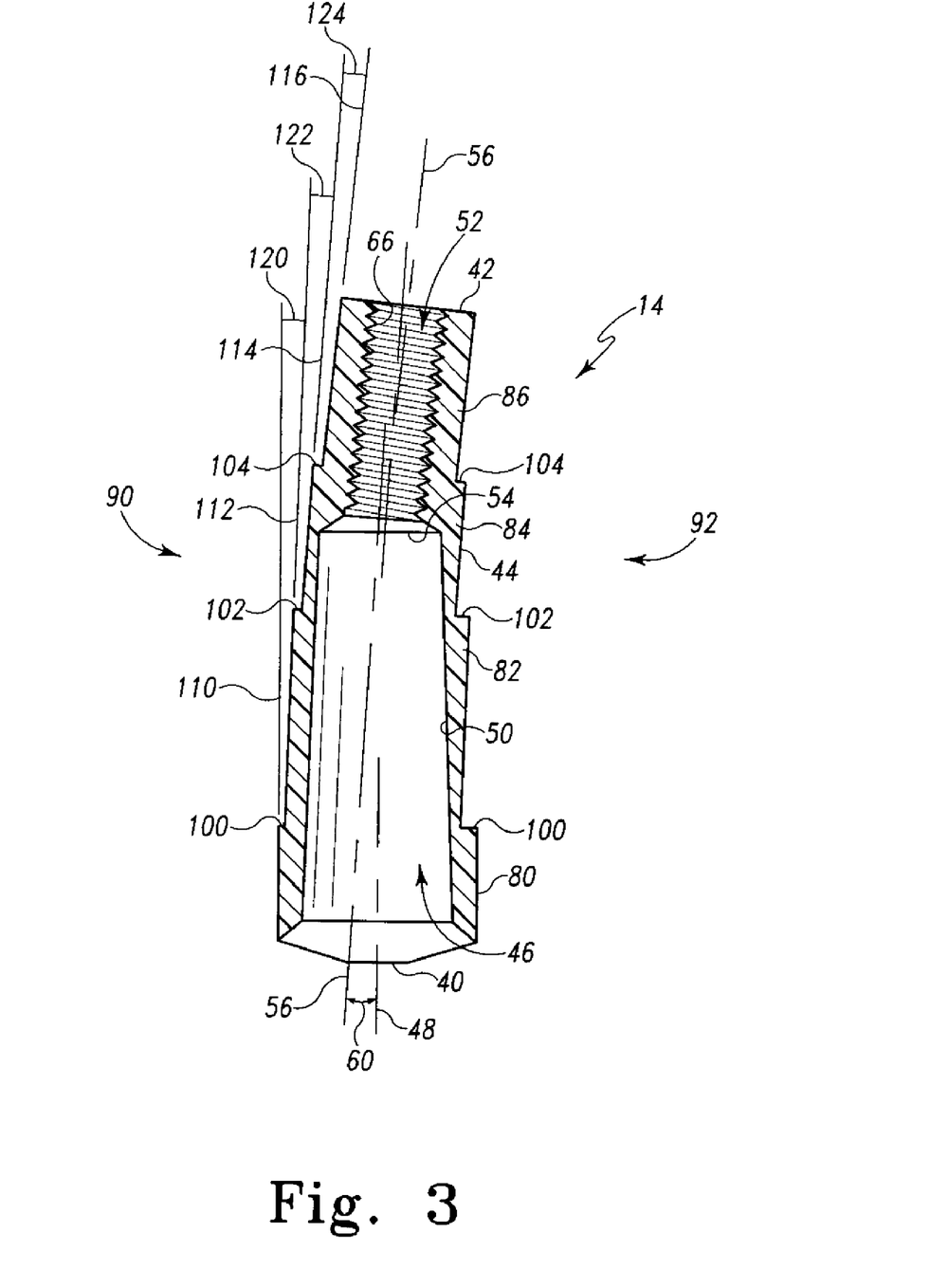
FIG. 3 is a side sectional view through the center sagittal plane of a femoral sleeve of the modular femoral joint prosthesis of FIGS. 1 and 2.
Figure 4:
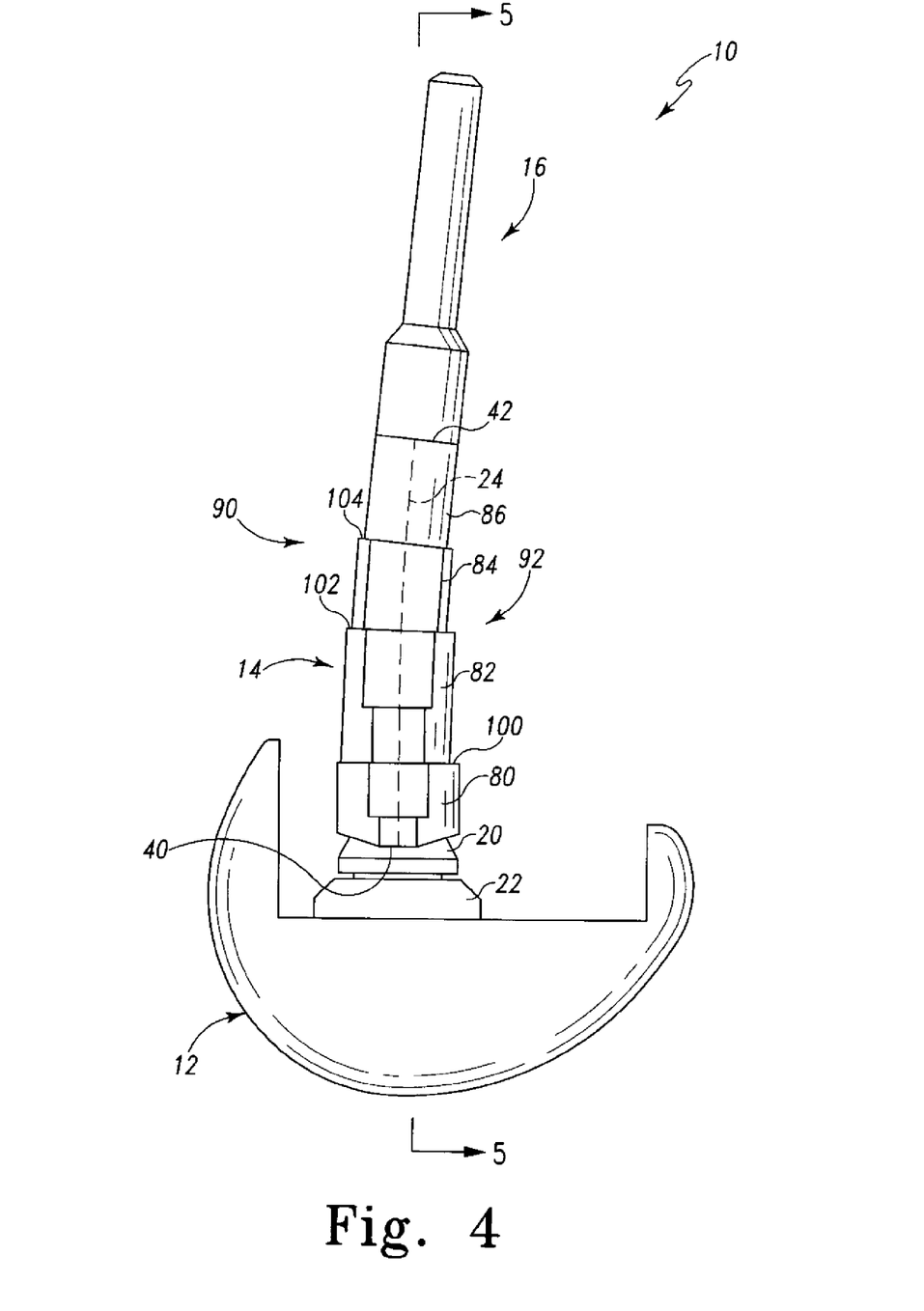
FIG. 4 is a side view of the assembled modular femoral joint prosthesis of FIGS. 1 and 2.

As shown in FIGS. 1-4 and 8, the femoral sleeve 14 is bowed posteriorly in the sagittal plane in order to more closely conform to the anatomic bow in the distal portion of a patient's femur. The femoral sleeve 14 is primarily used in knee replacement surgeries where a large cavity defect of the distal femur requires the additional fixation provided by the sleeve. What is meant herein by the term "bowed" as it applies to a femoral sleeve is the generally arcuate shape produced by an imaginary line or collection of line segments extending through the center of the femoral sleeve from a distal end of the sleeve to a proximal end of the sleeve. For example, as is shown in FIG. 4, an imaginary line 24 extends through the center of the femoral sleeve 14 from a distal end surface 40 of the femoral sleeve 14 to a proximal end surface 42 to define a generally arcuate or curved shape.

Figure 8:
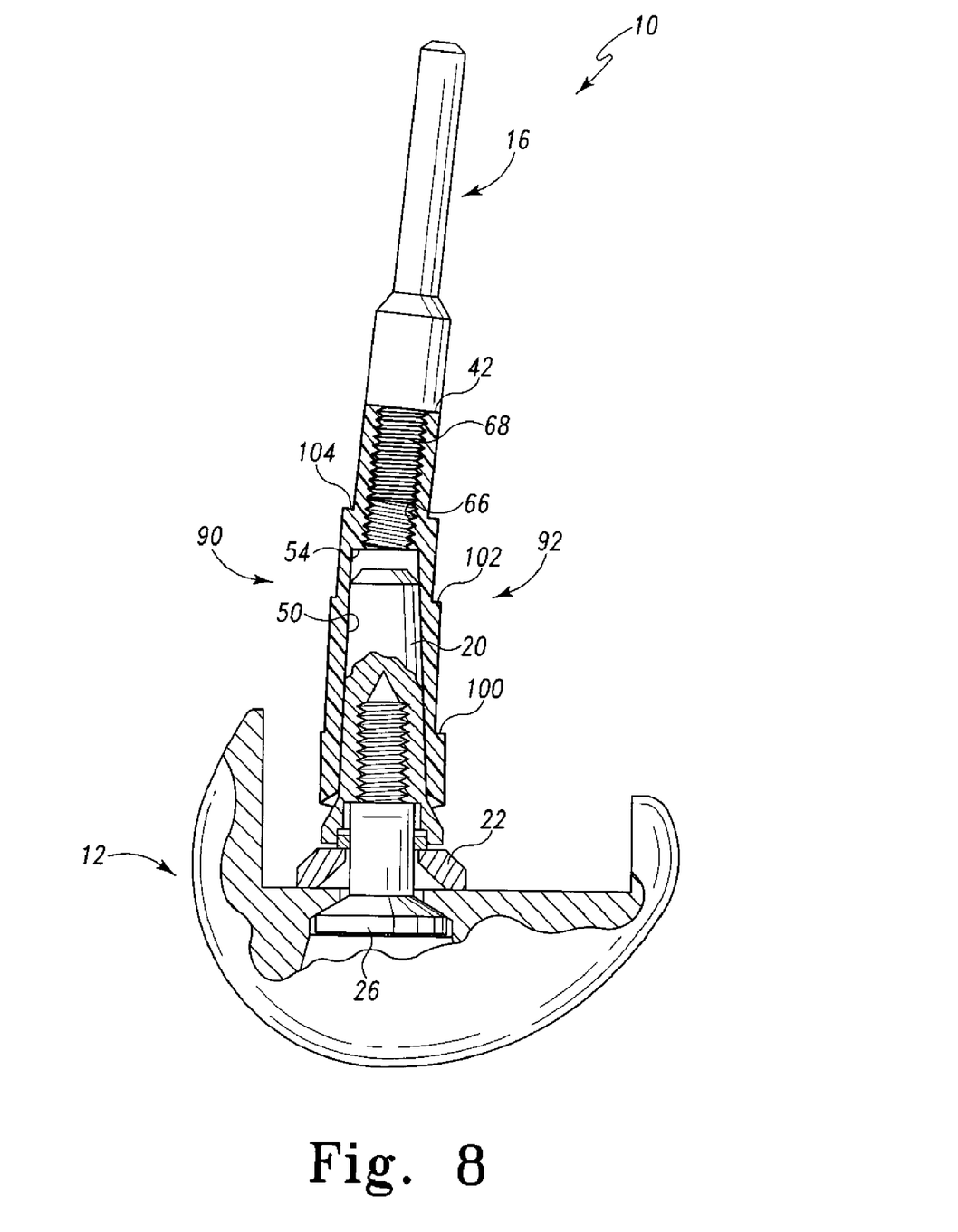
FIG. 8 is a side sectional view taken along line 8-8 of FIG. 7.

Looking now to FIG. 3, the femoral sleeve 14 includes a body having a first, or distal, bore 46 formed therein. The bore 46 is open to the distal end surface 40 of the femoral sleeve 14 and extends proximally into the body of the femoral sleeve 14. Illustratively, a first longitudinal axis 48, shown in FIG. 3, extends through the center of the distal bore 46. The distal bore 46 is defined by a tapered inner surface 50 such that the distal bore 46 defines a female taper. Specifically, the distal bore 46 defines a female Morse taper configured to receive the tapered stem 20 of the femoral component 12, as shown in FIGS. 5 and 8.

The femoral sleeve 14 further includes a second, or proximal, bore 52. The proximal bore 52 is open to the proximal end surface 42 of the sleeve 14 and extends distally into the body of the sleeve 14. In the illustrative femoral sleeve 14, the distal bore 46 and the proximal bore 52 are open to one another; however, it is within the scope of this disclosure to include a femoral sleeve having distal and proximal bores formed therein which are not open to one another. An internal shoulder 54 of the sleeve 14 is defined between the distal bore 46 and the proximal bore 52. Illustratively, a second longitudinal axis 56, shown in FIG. 3, extends through the center of the proximal bore 52 and intersects the longitudinal axis 48 of the distal bore 46. In other words, the longitudinal axes 48, 56 are not coaligned and are not parallel to each other. The proximal bore 52 is angled with respect to the distal bore 46 to define an acute angle of intersection 60 between the longitudinal axes 48, 56. In one illustrative example, the angle 60 is between 2°-5°, and in another illustrative example, the angle 60 is approximately 3°. However, it is within the scope of this disclosure to include a femoral sleeve having distal and proximal bores positioned at any suitable acute angle relative to each other.

Further illustratively, the longitudinal axis 48 of the distal bore 46 is generally vertical. In other words, the longitudinal axis 48 of the distal bore 46 is perpendicular to a plane defined by the distal end surface 40 of the sleeve 14 and is generally coaligned with an imaginary vertical line perpendicular to this plane. Alternatively, the longitudinal axis 48 of the distal bore 46 may not be perpendicular to the plane defined by the distal end surface 40 of the sleeve 14.

The inner surface of the proximal bore 52 of the sleeve 14 is threaded to define internal threads 66. As shown in FIGS. 1, 2, 5, and 8, the femoral stem 16 includes a threaded distal shaft 68 configured to be threaded into the proximal bore 52 in order to couple the femoral stem 16 and the femoral sleeve 14 together. Illustratively, while the entire inner surface of the proximal bore 52 is threaded and the entire outer surface of the distal shaft 68 of the stem 16 is threaded, it is within the scope of this disclosure for only cooperating portions of the bore 52 and the distal shaft 68 to be threaded.

Figure 6:
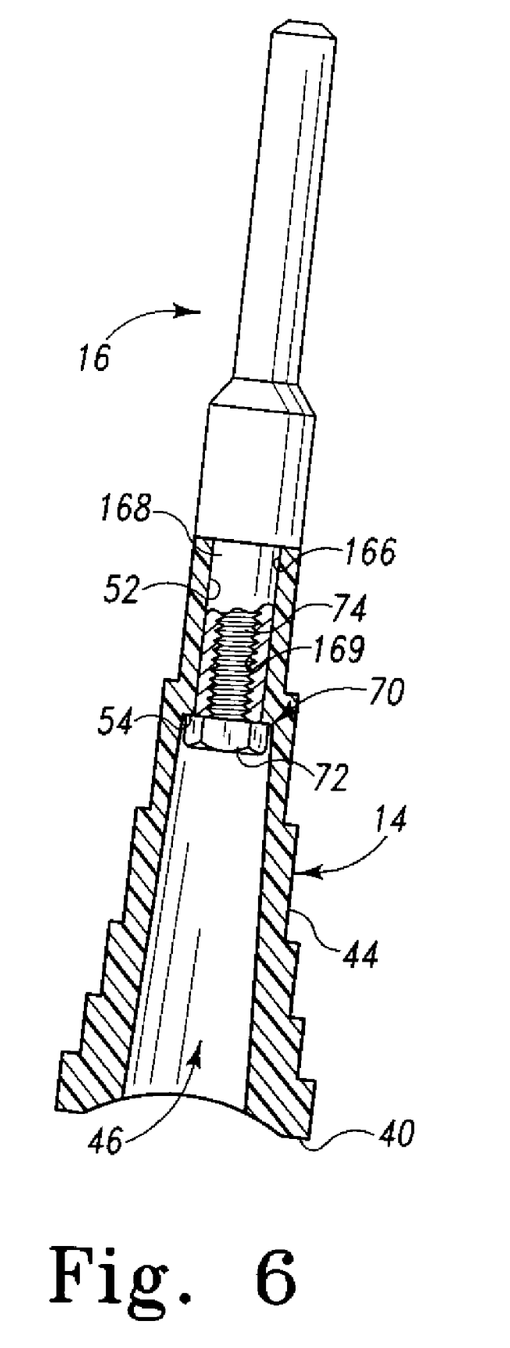
FIG. 6 is a front, sectional view of an alternative stem component coupled to the femoral sleeve of the modular femoral joint prosthesis.

In an alternative embodiment, the inner surface of the bore 52 is not threaded, as shown in FIG. 6 for example. A threaded screw 70 is positioned within the bores 46, 52 of the sleeve 14. In particular, a head 72 of the screw 70 is positioned within the distal bore 46 while the shaft 74 of the screw 70 is positioned within the proximal bore 52 such that a bottom surface of the head 72 of the screw 70 abuts the inner shoulder 54 of the sleeve 14. In this embodiment, an inner surface 166 of the bore 52 is smooth, or non-threaded, while the distal shaft 168 of the stem component 16 includes a threaded bore 169 configured to receive the threaded shaft 74 of the screw 70 therein in order to couple the femoral sleeve 14 and the femoral stem 16 together. In yet another alternative embodiment (not shown), the inner surface of the proximal bore 52 may define a female Morse taper while the outer surface of the distal shaft of the stem component 16 may define a male Morse taper configured to be press-fit into the proximal bore 52. It is within the scope of this disclosure to use other suitable means of coupling the sleeve 14 and the stem 16 together. Similarly, in addition to a Morse taper fit, it is within the scope of this disclosure to include other suitable means of coupling the post 20 and the sleeve 14 together.

The femoral sleeve 14 includes an anterior side 90, a posterior side 92, a medial side 94, and a lateral side 96. Looking again to FIGS. 3 and 5, an outer surface 44 of each of the anterior side 90, posterior side 92, medial side 94 and lateral side 96 of the sleeve 14 is contoured, or more specifically, is stepped to define steps or ledges 100, 102, 104. Each of the ledges 100, 102, 104 defines a corresponding first (or distal), second, third, and fourth (or proximal) stepped section 80, 82, 84, 86. For example, the ledge 100 separates the first section 80 from the second section 82, ledge 102 separates the second section 82 from the third section 84, and the ledge 104 separates the third section 84 from the fourth section 86. Illustratively, the bowed outer surface 44 of the femoral sleeve 14 is created by angling each of the stepped sections 80, 82, 84, 86 relative to each other. In other words, when viewed in the sectional view of FIG. 3 taken through the center sagittal plane of the sleeve 14, an imaginary line extending along an inferior/superior direction along the anterior surface 90 of each stepped section 80, 82, 84, 86 intersects each of the other imaginary lines extending along the anterior surfaces 90 of each of the other stepped sections 80, 82, 84, 86. Similarly, when viewed in cross section through the center sagittal plane of the femoral sleeve 14, any imaginary line extending along an inferior/superior direction along the posterior surface 92 of each stepped section 80, 82, 84, 86 intersects each of the other imaginary lines extending along the posterior surface 92 of each of the other stepped sections 80, 82, 84, 86. For example, the first stepped section 80 defines a first imaginary line 110 extending along the anterior surface 90 of the first stepped section 80, as shown in FIG. 3. Similarly, the second stepped section 82 defines a second imaginary line 112, the third stepped section 84 defines a third imaginary line 114, and the fourth stepped section 86 defines a fourth imaginary line 116.

A first acute angle of intersection 120 is defined between the first and second imaginary lines 110, 112. A second acute angle of intersection 122 is defined between the second and third imaginary lines 112, 114. Similarly, a third acute angle of intersection 124 is defined between the third and fourth imaginary lines 114, 116. Illustratively, each of the first, second, and third acute angles of intersection 120, 122, 124 is approximately 1° such that a total bow of the femoral sleeve 14 is approximately 3°.

Illustratively, the ledges 100, 102, 104 of the contoured outer surface 44 of the sleeve 44 each define a plane. Similar to the imaginary lines 110, 112, 114, 116 discussed above, each of the planes defined by the ledges 100, 102, 104 intersects each of the other planes defined by each of the other ledges 100, 102, 104 to define acute angles of intersection (not shown) therebetween. Accordingly, while the femoral sleeve 14 described herein is configured to define the imaginary lines 110, 112, 114, 116 discussed above which intersect each other as well the ledge planes discussed above which also intersect each other, it is within the scope of this disclosure to include a bowed femoral sleeve which includes only one of the intersecting imaginary lines or the intersecting ledge planes.

Further, it is within the scope of this disclosure for the femoral sleeve 14 to include more than four stepped sections. For example, a bowed femoral sleeve of the present disclosure may include any number of stepped sections (i.e., more than or less than four stepped sections) in order to suit the particular needs of the specific joint replacement surgery for which the femoral sleeve is being used. It is also within the scope of this disclosure for the acute angles of intersection defined by the stepped sections to be greater than or less than 1°. Moreover, one or more of the acute angles of intersection defined by the stepped sections may have different from one or more of the other acute angles of intersection. Further, while the proximal end surface 42 of the illustrative femoral sleeve 14 disclosed herein defines a plane which is not parallel with a plane defined by the distal end surface 40, it is within the scope of this disclosure to include a femoral sleeve having proximal and distal end surfaces defining planes which are parallel to each other.

As noted above, the femoral sleeve 14 is bowed posteriorly in the sagittal plane in order to accommodate the naturally bowed nature of the distal femur, as shown in FIGS. 2, 3, 4, and 8. However, it is also within the scope of this disclosure to include a femoral sleeve bowed anteriorly in the sagittal plane as well as medially or laterally in the coronal plane. Further, although the bowed sleeve is described herein in the exemplary context of a femoral knee prosthesis, it is within the scope of this disclosure to incorporate a bowed sleeve into the design of other types of joint prostheses in order to accommodate the natural bow of the particular bone into which the sleeve component is being implanted. Such bowed sleeves may be bowed posteriorly, anteriorly, medially, and/or laterally to fit the needs of a given prosthesis design. Finally, although the illustrated modular femoral joint prosthesis 10 includes a femoral component 24 adapted for a right knee, the concepts of the present disclosure are suitable for use with a femoral component adapted for a left knee. Along this line, the femoral sleeve 14 described herein may be used with either a right or left femoral component without modification thereto.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, although specific data rate values and ranges and specific frequency values and ranges have been disclosed in various embodiments, it should be appreciated that data rates and/or frequencies near such values may be in used in other embodiments.

There are a plurality of advantages of the present disclosure arising from the various features of the systems and methods described herein. It will be noted that alternative embodiments of the systems and methods of the present disclosure may not include all of the features described yet still benefit from at least some of the advantages of such features. Those of ordinary skill in the art may readily devise their own implementations of the systems and methods that incorporate one or more of the features of the present invention and fall within the spirit and scope of the present disclosure as defined by the appended claims.

The invention claimed is:

1. A modular femoral joint prosthesis comprising:
   a femoral sleeve having a distal end, a proximal end, a first bore formed in the distal end, and a second bore formed in the proximal end, the femoral sleeve being bowed in a posterior direction such that the distal end is positioned anterior to the proximal end,
   a femoral component having an articulating condylar surface,
   a post having a first end secured to the femoral component and a second end positioned in the first bore of the femoral sleeve, and
   a femoral stem configured to be implanted within the intermedulary canal of the distal end of a femur, the femoral stem having a first end positioned in the second bore of the femoral sleeve and a second end extending proximally away from the femoral sleeve.

2. The modular femoral joint prosthesis of claim 1, wherein the first bore defines a first longitudinal axis and the second bore defines a second longitudinal axis which intersects the first longitudinal axis to define an acute angle of intersection therebetween.

3. The modular femoral joint prosthesis of claim 1, wherein:
the second bore defines a second longitudinal axis, and
the second longitudinal axis intersects an imaginary line extending perpendicularly from a plane defined by a distal surface of the femoral sleeve to define an acute angle of intersection therebetween.

4. The modular femoral joint prosthesis of claim 3, wherein the first bore defines a first longitudinal axis coaligned with the imaginary line.

5. The modular femoral joint prosthesis of claim 3, wherein the first bore defines a first longitudinal axis which intersects the imaginary line.

6. The modular femoral joint prosthesis of claim 3, wherein the acute angle of intersection is between 2-5°.

7. The modular femoral joint prosthesis of claim 3, wherein the acute angle of intersection is approximately 3°.

* * * * *